United States Patent [19]

Lynch et al.

[11] Patent Number: 4,860,757
[45] Date of Patent: Aug. 29, 1989

[54] GUIDEWIRE ADVANCEMENT SYSTEM

[75] Inventors: Arthur S. Lynch, Westwood; A. Walter MacEachern, Woburn, both of Mass.

[73] Assignee: Medical Parameters, Incorporated, Woburn, Mass.

[21] Appl. No.: 114,451

[22] Filed: Oct. 28, 1987

[51] Int. Cl.<sup>4</sup> ............................................. A61B 6/00
[52] U.S. Cl. ..................................... 128/657; 128/772; 604/164
[58] Field of Search ..................... 128/1 R, 657, 772; 604/158, 159, 160, 163, 164

[56] References Cited

U.S. PATENT DOCUMENTS

| 3,561,445 | 2/1971 | Katerndahl | 604/159 |
| 3,995,628 | 12/1976 | Gula et al. | 128/214.4 |
| 4,003,369 | 1/1977 | Heilman et al. | 128/2 M |
| 4,080,706 | 3/1978 | Heilman et al. | 29/173 |
| 4,160,451 | 7/1979 | Chittenden et al. | 128/214.4 |
| 4,342,313 | 8/1982 | Chittenden et al. | 128/214.4 |
| 4,397,091 | 9/1983 | Gustavsson et al. | 33/127 |
| 4,425,908 | 1/1984 | Simon | 128/1 R |
| 4,534,363 | 8/1985 | Gold | 128/772 |
| 4,650,472 | 3/1987 | Bates | 604/158 |
| 4,676,249 | 6/1987 | Arenas et al. | 128/657 |

Primary Examiner—Max Hindenburg
Assistant Examiner—Randy Citrin
Attorney, Agent, or Firm—Hamilton, Brook, Smith & Reynolds

[57] ABSTRACT

A guidewire advancement system for inserting catheter guidewires into blood vessels, and more particularly a guidewire dispensing system for the controlled sterile insertion of a coiled spring guidewire to avoid infection of the patient. The system provides for the transmission of an electrical signal by the guidewire to determine its location within the body.

4 Claims, 3 Drawing Sheets

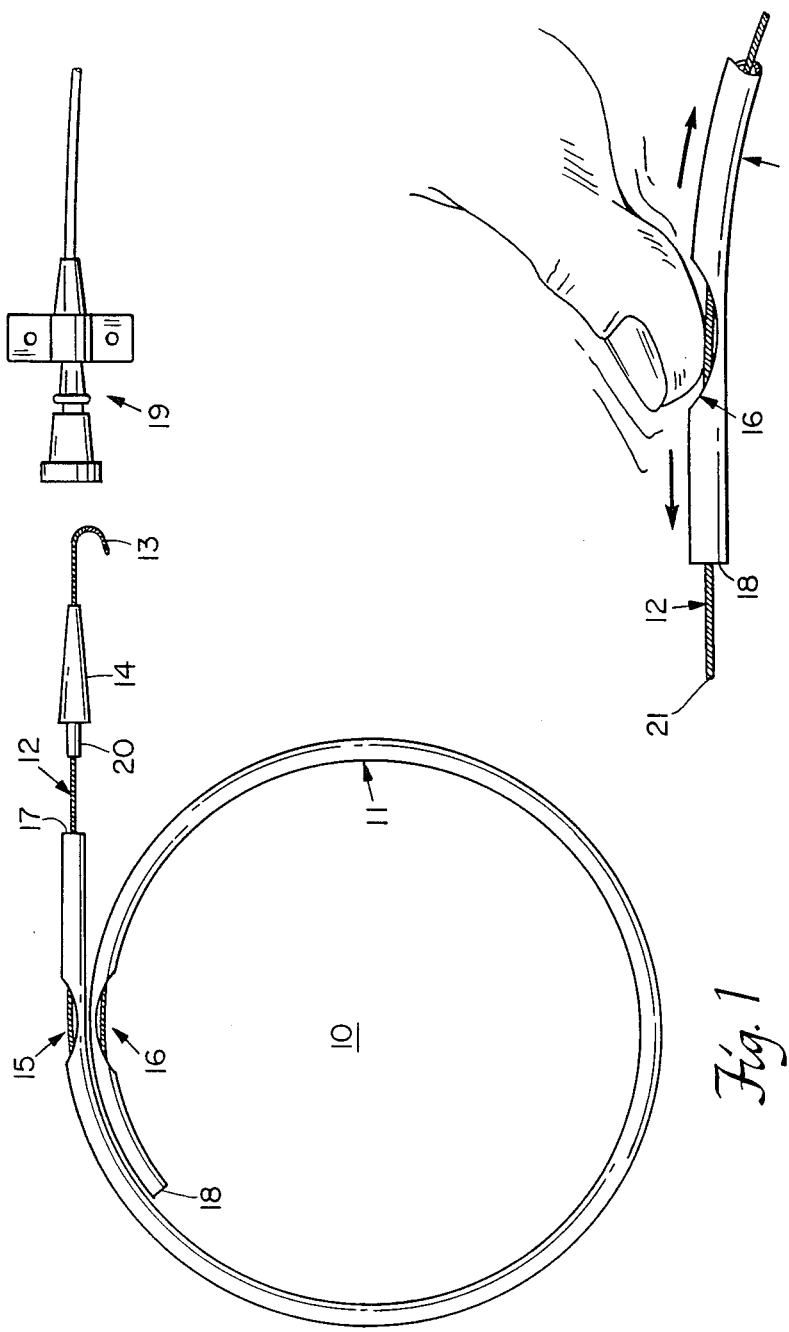

GUIDEWIRE ADVANCEMENT SYSTEM

BACKGROUND OF THE INVENTION

The invention relates to devices for the insertion of catheter guidewires into blood vessels. A guidewire is inserted so that a catheter, which is coaxially engaged along the guidewire, can be slidably inserted into the blood vessel. The guidewire is then withdrawn, and the catheter is ready for further positioning and use. It is imperative that guidewires be inserted without contamination of the sterile field to avoid unnecessary infection of the patient.

Guidewires are generally comprised of a coiled spring guide with a distal tip and one or more wires running longitudinally within the spring. Such guidewire constructions are disclosed in U.S. Pat. Nos. 4,003,369 and 4,676,249. Catheters are generally hollow, flexible tubes used to convey liquids or other instruments to a desired location in the body.

Existing systems for guidewire insertion suffer from continued problems arising from the lack of ease in manipulation and the exposure during insertion to a non-sterile environment. Normally, a guidewire is removed completely from its package prior to use, is wound in the physicians hand and inserted through a needle extending into the patient's artery, or through a cannula into some other body cavity. Three or more hands are required to hold the needle stationary while the "J" guidewire is pulled through a straightener, then pushed through the port in the needle. The inadvertant extension of the guidewire prior to insertion and the awkwardness of manipulation during insertion leads to contamination of the sterile field and the patient's blood stream. It is also desirable that the physician or operator be able to tactilely sense the progress of the guidewire tip during insertion to insure better control.

SUMMARY OF THE INVENTION

A catheter guidewire is packaged for use in a hollow tube or casing which maintains a sterile environment for the guidewire prior to use. The guidewire is displaceable through an outlet at one or both ends of the tube for insertion into the desired artery or body cavity.

An aperture in the casing is located adjacent to the outlet so as to provide access to the guidewire surface. By applying a lateral frictional force to the surface of the guidewire in the direction of the outlet, the guidewire can be displaced through the narrow tube and the outlet.

A second tube attached to the outlet and disposed to receive the guidewire as it exits the casing can be used to straighten a "J" guidewire prior to entering a canal through a needle or cannula. In a preferred embodiment of the invention, the aperture for frictionally displacing the guidewire can be located in the straightening tube. The invention thus provides a means for maintaining a sterile environment during storage and insertion of the guidewire. Only one hand is necessary to operate the dispensing mechanism while the desired sensitivity to guidewire placement in maintained.

In another preferred embodiment, a moveable member is positioned over the aperture to maintain a sterile environment for the guidewire while at the same time providing the frictional force to displace the guidewire. This moveable member can be hand actuated rollers or a slidable bar or any other suitable mechanical device that maintains the tactile sense of the operator with regard to directing the guidewire through the system. The member which can be manually depressed to frictionally engage the guidewire surface. The moveable member can also be placed in a housing used to hold the two ends of the casing.

One embodiment of the system provides for the transmission of an electrocardiographic signal through the guidewire to determine the position of the distal end of the guidewire that has been inserted into a body canal. The housing that holds the frictionally engaging member referenced above is positioned about the aperture and used to transmit an internally generated electrical signal onto the conductive guidewire element.

The above, and other features of the invention, including various novel details of construction and combination of parts, will now be more particularly described with reference to the accompanying drawings and pointed out in the claims. It will be understood that the particular guidewire advancement system embodying the invention is shown by way of illustration only and not as a limitation of the invention. The principle features of this invention may be employed in varied embodiments without departing from the scope of the invention. For example, the device can be utilized in the catheterization of any body cavity or artery, or alternatively in any veterinary applications involving catheterization procedures.

BRIEF DESCRIPTION OF THE DRAWINGS

FIG. 1 illustrates a plan view of the guidewire system generally;

FIG. 2 schematically illustrates a close up view of the guidewire aperture operated by hand;

DETAILED DESCRIPTION OF THE INVENTION

Figure 3:
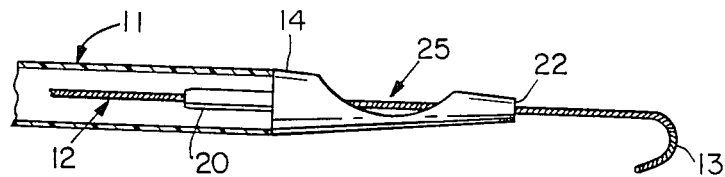
FIG. 3 illustrates a plan view of an alternative embodiment where the aperture is located in the guidewire straightener.

A preferred embodiment of the guidewire advancement system 10 is illustrated in FIG. 1. A flexible hollow tube 11 can be disposed in the shape of a curve or loop(s) as depicted to facilitate ease of operation. A guidewire 12 of standard coiled spring design is slidably inserted into tube 11. The guidewire 12 can enter or exit tube 11 through either of the two open ends 17 and 18. The guidewire 12 is inserted into a vein or artery through a needle, or canal or cavity by a cannula 19.

One end of the guidewire 12 can be formed in the shape of a flexible "J" 13. The "J" 13 may be straightened by pulling the end of the guidewire bearing the "J" back into the straightening element 14. The straightener 14 has a narrow hollow tube to which the "J" must conform upon entry therein. The straightener 14 is attached to tube 11 by inserting a small diameter portion 20 of straightener 14 into the port 17. The outer diameter of portion 20 is chosen so that it fits snugly into the hollow tube 11 at 17. The purpose of the "J" 13 is to permit the guidewire operator to more precisely direct the insertion of the guidewire to the precise arterial location desired. As the guidewire proceeds along the inside of an artery there are commonly two or more paths for it to follow. The operator, using the tension in the straightened "J" to return to its preferred shape, can direct the guidewire down the desired artery path. Simply by rotating the guidewire within the cannula 19, the "J" 13 will be redirected as desired.

Existing guidewire packages typically involve the complete removal of the guidewire from the tubing in which they are stored before use. This often exposes the guidewire to non-sterile environments thereby risking the infection of the patient when the exposed guidewire is inserted into the bloodstream.

The present invention claims the use of apertures 15 and 16 located adjacent the two end ports 17 and 18. These apertures provide access to the guidewires 12 so that it may be inserted into the bloodstream without being first removed from its storage tube 11 or jacket. The apertures 15 and 16 permit the use of the guidewire to be confined within the sterile field thereby substantially reducing the risk of unnecessary infection.

FIG. 2 illustrates how the apertured guidewire system may be operated by hand. by inserting his or her thumb into the aperture 16, the operator frictionally engages the guidewire 12, and can either advance or retract it as shown. This design permits one handed operation that is sensitive to guidewire placement. Aperture 16 may be used, as opposed to aperture 15 in FIG. 1, where the operator prefers to use the straight end 21 of the guidewire through port 18, instead of the "J" shaped end 13.

FIG. 3 illustrates another preferred embodiment of the invention where the straightener 14 is provided with aperture 25. The guidewire 12 can be manipulated through aperture 25 directly adjacent the guidewire exit point 22, instead of further back along the tube 11 at aperture 15 in FIG. 1.

Figure 4:
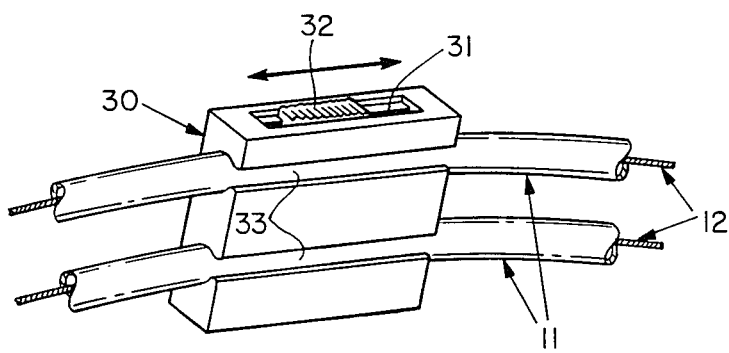
FIG. 4 illustrates a perspective view of a guidewire advancement system using a slidable bar.
Figure 5:
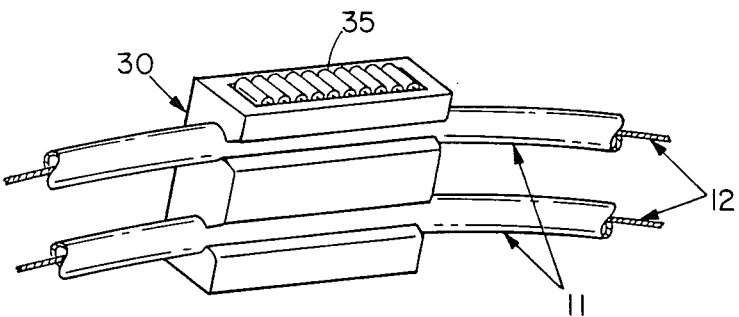
FIG. 5 illustrates a perspective view of a guidewire advancement system using rollers.

To further isolate the guidewire from exposure to non-sterile environments the apertures 15 and 16 can be enclosed with an element 30 as illustrated in FIGS. 4 and 5. The element 30 is used to hold the two ends of the tube 11 in the shape of a loop as shown in FIG. 1. The two ends of tube 11 are both snapped into the two parallel partially open tubes 33 extending through element 30 such that the apertures 15 and 16 (not shown) are completely enclosed.

A rectangular opening 31 can be made in the element 30 opposite the apertures (not shown) in tube 11. A slidable cam or bar 32 may be fitted into opening 31 that can be manually depressed to frictionally engage the guidewire. By positioning the cam 32 at one end of the opening 31, the guidewire 12 may be advanced through the tube 11 in one direction. By depressing the cam 32 to engage the guidewire, the operator slides the cam 32 to the other end of the opening 31, releasing the cam 32 from its depressed position, moving the cam 32 back to its position at the opposite end of the opening 31, and then repeating this sequence of steps until the guidewire is in the desired location.

FIG. 5 illustrates a further embodiment of the invention in which a number of rollers 35 may be depressed to engage the guidewire 12 through an enclosed aperture in tube 11. These rollers frictionally engage the guidewire 12 such that their manually actuated rotation causes the guidewire to be pushed through tube 11 for insertion into the artery.

Both the cam 32 of FIG. 4 and the rollers 35 of FIG. 5 may be held within member 30 by resilient means which lift the cam 32 or rollers 35 off of the guidewire 12 when not manually depressed against it by the operator. This resilient means renders the cam 32 or rollers 35 easier to cycle a number of times to fully extend the guidewire.

Figure 6:
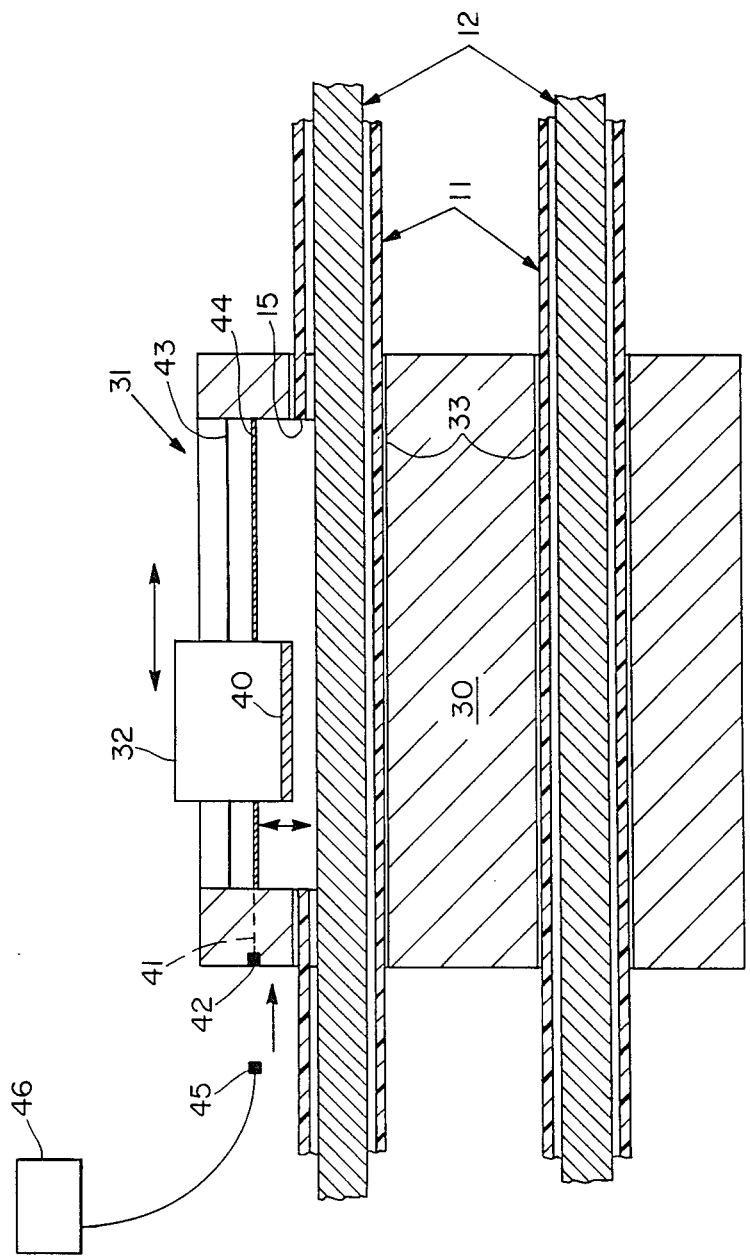
FIG. 6 is a magnified cross-sectional view illustrating the use of an external monitor that displays an internally generated electrical signal transmitted along the guidewire that is employed in determining the position of the guidewire.

Another preferred embodiment is illustrated in the magnified cross sectional view of FIG. 6. As in FIG. 4, a conductive guidewire 12 is displaceable through tubing 11, that is held by a housing 30. A slideable bar 32 is configured to move back and forth within an opening 31. The bar 32 is supported by a track 43. A lower portion of the track 43 incorporates a conductive lining 44 in conductive contact with a conductive pad 40 mounted on the underside of bar 32. The track 43 and attached lining 44 are flexible thereby permitting the bar 32 to be depressed manually by the operator such that the pad 40 comes in contact with the guidewire through aperture 15 of tube 11. The lining 44 is in conductive contact with an outlet 42 by wire 41. The outlet 42 is mated with an external plug 45 connected to an external monitor 46. The electrical signal generated by an internal organ such as the human heart transmits a signal through the guidewire 12 to pad 40 when the bar 32 is depressed. This signal is transmitted through the distal tip of the guidewire that has been inserted into a bodily canal or artery to determine the location of the distal tip within the body being catheterized. As the tip approaches the heart muscle, it transmits the electrical current generated about the heart along the guidewire through the engaging means of the housing to be displayed by the monitor 46. This system provides for a more precise positioning of the guidewire as well as the catheter while at the same time providing for the sterile insertion of the guidewire.

We claim:

1. A catheter guidewire advancement system comprising:
   a hollow casing for housing a catheter guidewire with a first outlet at one end and a second outlet;
   straightener means for straightening the guidewire such that the straightener is disposed to receive said guidewire as it is dispensed through the first outlet; and
   a first aperture for exposing a portion of the guidewire and a second aperture adjacent the second outlet such that a frictional force applied laterally to the guidewire through the first or second aperture will displace the guidewire relative to the casing and through the first or second outlet.

2. A method of using a catheter guidewire advancement system comprising the steps of:
   placing a cannula into a body lumen;
   manually engaging, without intervening mechanical means, a guidewire directly through an aperture in a guidewire advancement system comprising a guidewire casing; and
   inserting the guidewire into the body by manually applying a lateral frictional force to the guidewire through the aperture in the casing to displace the guidewire relative to the casing and through the cannula into the body lumen.

3. A method of using a catheter guidewire advancement system as defined in claim 2 wherein the aperture is located in the casing adjacent an outlet through which the guidewire is displaced.

4. A method of using a catheter guidewire advancement system as defined in claim 2 wherein said manual engaging step is followed by the step of retracting the guidewire into a straightener by applying a lateral frictional force to the guidewire through the aperture.

* * * * *